(12) United States Patent
Ziv et al.

(10) Patent No.: US 6,269,704 B1
(45) Date of Patent: Aug. 7, 2001

(54) BLOOD SAMPLING DEVICE

(75) Inventors: David Ziv, Baram; Tomer Gil, Yiron, both of (IL)

(73) Assignee: Elcam Plastic Cooperative Agricultural Association Ltd., Baram (IL)

( * ) Notice: Subject to any disclaimer, the term of this patent is extended or adjusted under 35 U.S.C. 154(b) by 0 days.

(21) Appl. No.: 09/623,918

(22) PCT Filed: Dec. 13, 1999

(86) PCT No.: PCT/IL99/00679

§ 371 Date: Nov. 6, 2000

§ 102(e) Date: Nov. 6, 2000

(87) PCT Pub. No.: WO00/41624

PCT Pub. Date: Jul. 20, 2000

(30) Foreign Application Priority Data

Jan. 12, 1999 (IL) .......................................... 128016

(51) Int. Cl.[7] ..................................................... G01N 1/14
(52) U.S. Cl. ..................................... 73/863.84; 73/864.74; 600/573; 604/32; 604/248
(58) Field of Search ........................... 73/863.81, 863.84, 73/864.74; 600/573, 578; 604/32, 33, 248, 249

(56) References Cited

U.S. PATENT DOCUMENTS

| Re. 36,273 | * | 8/1999 | Brannon | 600/578 |
|---|---|---|---|---|
| 4,105,500 | * | 8/1978 | Libman et al. | 195/103.5 M |
| 4,703,763 | * | 11/1987 | McAlister et al. | 128/765 |
| 4,796,644 | * | 1/1989 | Polaschegg | 128/760 |
| 4,838,855 | * | 6/1989 | Lynn | 604/49 |
| 4,865,583 | * | 9/1989 | Tu | 604/53 |
| 5,002,066 | * | 3/1991 | Simpson et al. | 128/760 |
| 5,288,290 |   | 2/1994 | Brody | 604/32 |
| 5,324,266 | * | 6/1994 | Ambrisco et al. | 604/125 |
| 5,549,569 | * | 8/1996 | Lynn et al. | 604/91 |
| 5,795,340 | * | 8/1998 | Lang | 604/283 |
| 5,916,201 | * | 6/1999 | Wilson, Jr. et al. | 604/248 |
| 5,947,911 | * | 9/1999 | Wong et al. | 600/573 |
| 5,961,472 | * | 10/1999 | Swendson et al. | 600/573 |
| 6,156,019 | * | 12/2000 | Langevin | 604/323 |

FOREIGN PATENT DOCUMENTS

| 1.091.965 | 4/1955 | (FR) . |
| 97/18748 | 5/1997 | (WO) . |

* cited by examiner

*Primary Examiner*—Daniel S. Larkin
*Assistant Examiner*—Charles D. Garber
(74) *Attorney, Agent, or Firm*—Nath & Associates PLLC; Gary M. Nath

(57) ABSTRACT

A liquid sampling device (10) comprising a housing (12) defining a confined volume (90) and fitted with an inlet port (22) and an outlet port (18) and a drawing member (30) formed with a conduit (38) and being displaceable between a flow position in which the conduit communicates between the inlet port and the outlet port, and a drawing position in which communication between the inlet port and the outlet port is interfered and wherein upon displacing the drawing member (3) into the drawing position, liquid is drawn into the confined volume (10) via the outlet port (18).

15 Claims, 6 Drawing Sheets

BLOOD SAMPLING DEVICE

FIELD OF THE INVENTION

The present invention is in the field of liquid sampling devices and in particular it is concerned with a blood sampling device for mounting on a tubing of an infusion set.

BACKGROUND OF THE INVENTION

In many medical procedures, an individual is connected to an infusion set for administration of medicaments and liquids. However, periodically it is required to obtain a blood sample from the individual for carrying out laboratory tests.

It is thus required that such blood samples contain only so-called fresh blood drawn from the patient, i.e. Without residual medicaments or liquids from the infusion set on the one hand and, on the other hand, be freshly drawn from the individual.

For this purpose, there are a variety of blood sampling devices which are typically used with a suitable blood drawing port or valve as known per se.

A blood sampling device must be capable of first obstructing flow through the infusion set and then drawing a sufficient amount of liquid residual in a portion of the tubing of the infusion set extending between the sampling device and the individual, where the sufficient amount is defined as being at least slightly more than the volume confined within said tubing portion.

Various blood sampling devices are disclosed, for example, in U.S. Pat. Nos. 4,673,386, 5,324,266, 4,105,500, 4,703,763, 4,838,855 and 5,002,066.

It is an object of the present invention to provide a novel and improved sampling device suitable for use in particular in conjunction with an infusion set.

SUMMARY OF THE INVENTION

In accordance with the present invention there is provided a blood sampling device typically to be mounted on an infusion set at a location essentially proximal to an end of the infusion set connected to the patient.

In accordance with a present invention there is provided a liquid sampling device comprising:
  a housing defining a confined volume and fitted with an inlet port and an outlet port;
  a drawing member formed with a conduit and being displaceable between a flow position in which said conduit communicates between the inlet port and the outlet port, and a drawing position in which communication between the inlet port and the outlet port is interfered and wherein upon displacing the drawing member into the drawing position liquid is drawn into the confined volume via said outlet port.

According to a preferred embodiment, the sampling device is further provided with a sealing member displaceable between a first position corresponding with the flow and drawing positions of the drawing member, and a second position in which the confined volume is sealingly disconnected from the outlet port. When the device comprises a sealing member, it is ensured that during sampling of a liquid from a line connected to the outer port, liquid drawn into the confined volume will not be sampled.

In accordance with an embodiment of the invention, there is provided a sampling port fitted on a tube portion connected to the outlet port, which in said tube portion may be integral or not with the sampling device. The sampling port may be any of a variety of sampling valves as known in the art.

In accordance with a preferred embodiment of the present invention, the housing comprises a cylindrical space; the drawing member and the sealing member each have a sector-like shape snugly received within the housing, the volume of both said drawing member and said sealing member together is less than the volume of the cylindrical space.

By a specific design of the preferred embodiment, the drawing member and the sealing member are rotatably displaceable within the housing about a common axis coaxial with an axis of the cylindrical space of the housing.

Preferably, there is provided a displacing element extending from the housing and useful for displacing the drawing member between its flow position and drawing position. The displacing element is articulated or integrally formed with the drawing member.

In order to retain either or both of the sealing member and the drawing member in either of their respective positions, there may be provided a retaining arrangement. By one application, the retaining arrangement is a snapping-type engagement formed between a wall of the housing and a respective wall portion of either or both of the sealing member and the drawing member.

Preferably, the confined volume comprises an airing port for venting the confined volume during displacement of the drawing member between its respective positions.

By one specific design, the inlet port and the outlet port are co-axially aligned. By other designs, an axis of the conduit within the drawing member extends at a plane essentially perpendicular to a plane of displacement of the drawing member.

In accordance with the preferred embodiment of the present invention, the sealing member is displaced between its first and second positions by displacing the drawing member which in turn is displaced by the displacing element.

The arrangement in accordance with the preferred embodiment of the present invention is such that at the flow position of the drawing member a first side wall thereof is flush with a first side wall of the sealing member; and at the first and second positions of the sealing member a second side wall thereof is flush with a second side wall of the drawing member.

Typically, the displacing element is snappingly articulated to the housing in a manner ensuring smooth rotation thereof.

BRIEF DESCRIPTION OF THE DRAWINGS

For better understanding, the invention will now be described by way of example only, with reference to some figures. It should be understood that the examples are provided for demonstrating the invention, but in no way it is intended to limit the invention to these specific embodiments.

FIGS. 2A–2C are planar cross-sectional views along line II—II of the blood sampling device of FIG. 1 in three consecutive operative positions, wherein:

FIG. 2A illustrates the device in a flow position;

FIG. 2B illustrates the device in a blood drawing position; and

FIG. 2C illustrates the device in a sealed position wherein fresh blood may be drawn through a sampling port;

FIGS. 5A and 5B are planar cross-sectional views along line V—V of the device of FIG. 4 in its assembled position, wherein:

FIG. 5A illustrates the device in the flow position; and

FIG. 5B illustrates the device in the drawing position.

DETAILED DESCRIPTION OF SPECIFIC EMBODIMENTS

Figure 1:
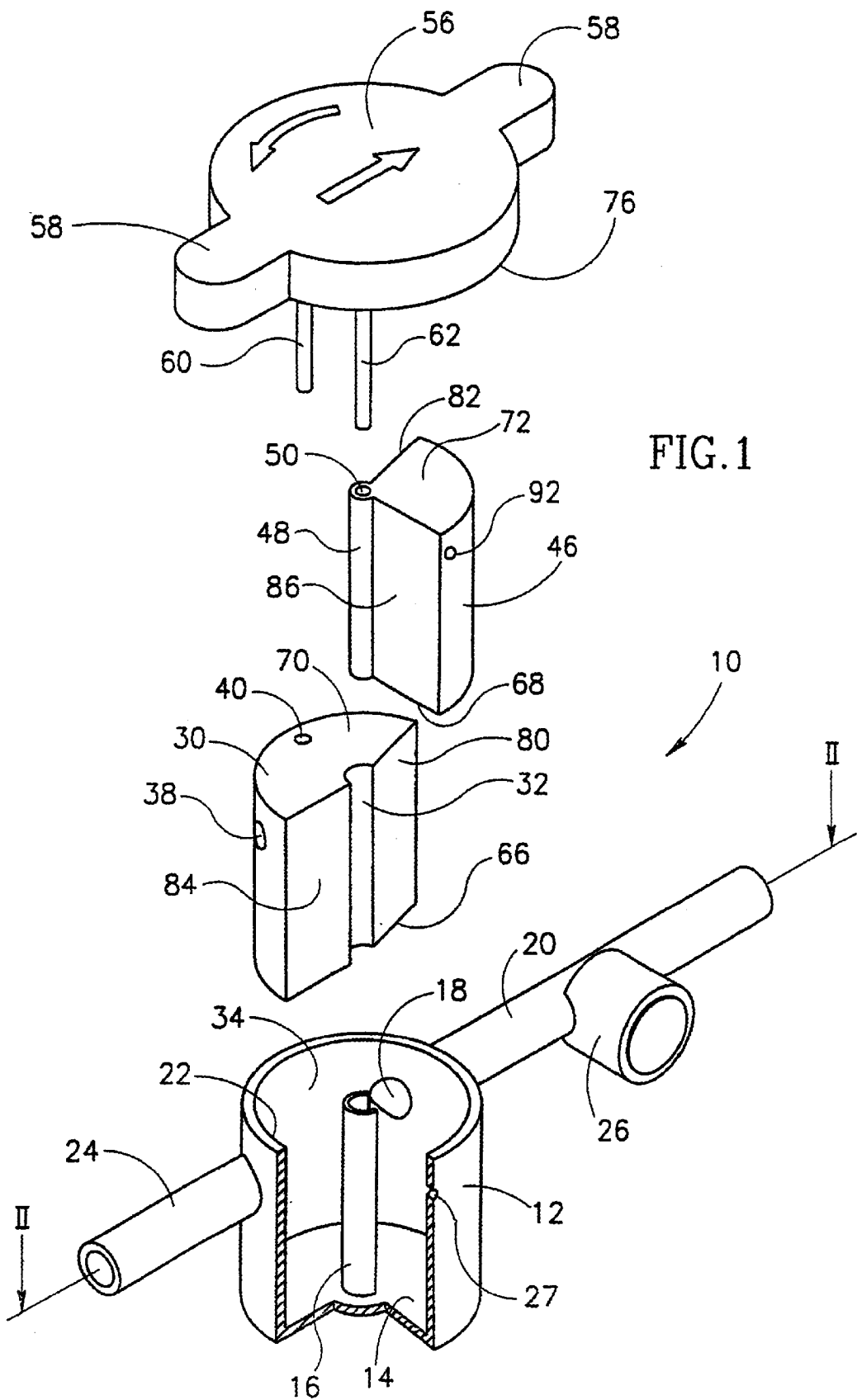
FIG. 1 is a perspective exploded view of a blood sampling device in accordance with a first embodiment of the present invention.

Attention is first directed to FIG. 1 of the drawings illustrating a blood sampling device generally designated 10 and comprising of a housing 12 being essentially cylindrical with a bottom wall 14 and a central hub 16 in the shape of an annular sector, typically being larger than 180° as will become apparent hereinafter.

Housing 12 is formed with an outlet port 18 fitted with an outlet tubing portion 20 and a co-axial inlet port 22 (best seen in FIG. 2) fitted with an inlet tubing portion 24. Outlet tubing 20 is fitted with a sampling port 26 which may have the form of any one of heretofore known such devices. Housing 12 is also provided with an airing port 27.

A drawing member 30 has a sector-like shape and a circular shaped recess 32 whereby the drawing member is snugly and rotatably received within cavity 34 of housing 12. As further noted, the drawing member 30 is formed with a through-going conduit 38 (best seen in FIG. 2) which in the assembled position, at a so-called flow position, extends between the inlet port 22 and the outlet port 18, as noticeable in FIG. 2A.

Drawing member 30 further comprises an engagement bore 40 for the purpose to become apparent hereinafter.

A sealing member 46 has a corresponding sector-like shape which is also adapted for snugly and rotatably being received within cavity 34 of housing 12. Sealing member 46 is fitted with a hub 48 rotatably receivable within hub 16 of housing 12. Hub 48 is formed with bore 50 which is co-axial with a longitudinal axis of the cylindrical housing 12.

Displacing element 56 generally has the shape of a disk with two manipulating projections 58 and has two projecting pins 60 and 62, the latter being co-axial, adapted for engagement with corresponding bores 40 and 50 of drawing member 30 and sealing member 46, respectively. Accordingly, in the assembled position, rotating the displacing element 56 entails rotational displacing of the drawing member 30 which in turn entails displacement of the sealing member 46 as will become apparent with reference to FIG. 2 hereinafter.

The arrangement is such that at the assembled position, the bottom surfaces 66 and 68 as well as top surfaces 70 and 72 of the drawing member 30 and sealing member 46, respectively, are flush with one another, whereby the bottom surfaces 66 and 46 are flush with the base wall 14 of housing 12 and the top surfaces 70 and 72 are flush with a bottom surface 76 of the displacing element 56.

It is also to be appreciated that first side walls 80 and 82 and second side walls 84 and 86 of the drawing member 30 and the sealing member 46, respectively are planar and as will become apparent hereinafter with reference to FIG. 2 are flush with one another in various positions. In some applications the side walls may be other than planar, as can readily be understood.

It will further be noted that although not seen in the figures, the housing 12 and the sector-like shaped drawing member 30 and sealing member 46 slightly taper downwardly, i.e. their bottom surfaces are slightly smaller than their top surfaces, this owing to some manufacturing and assembling considerations, as known in the art. However, this is merely a preferred design.

Figure 2A:
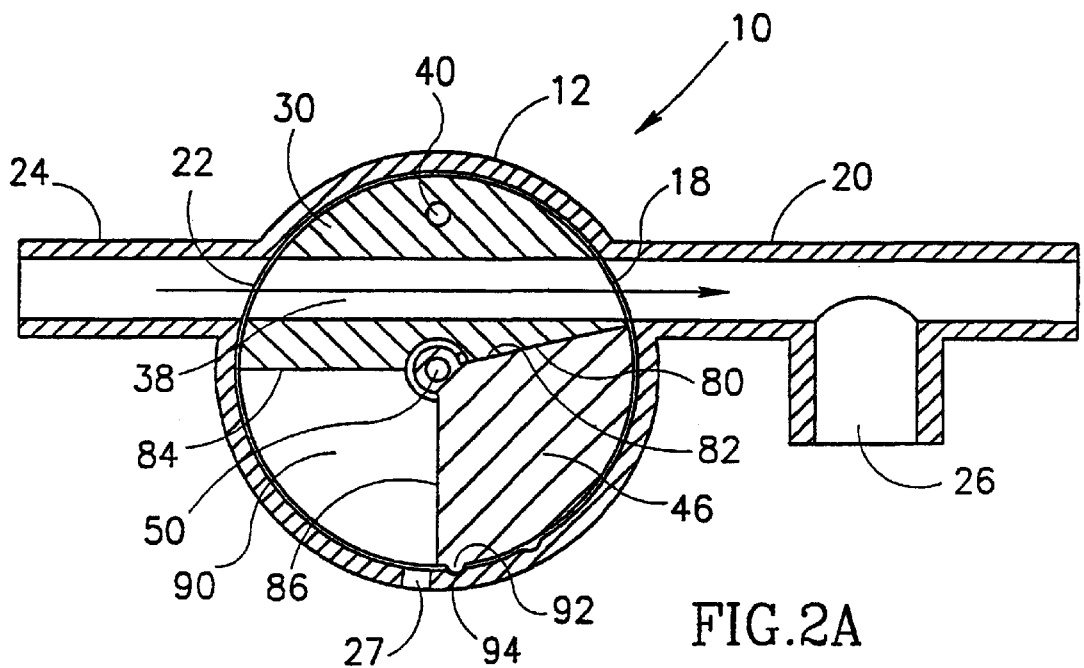
Figure 2B:
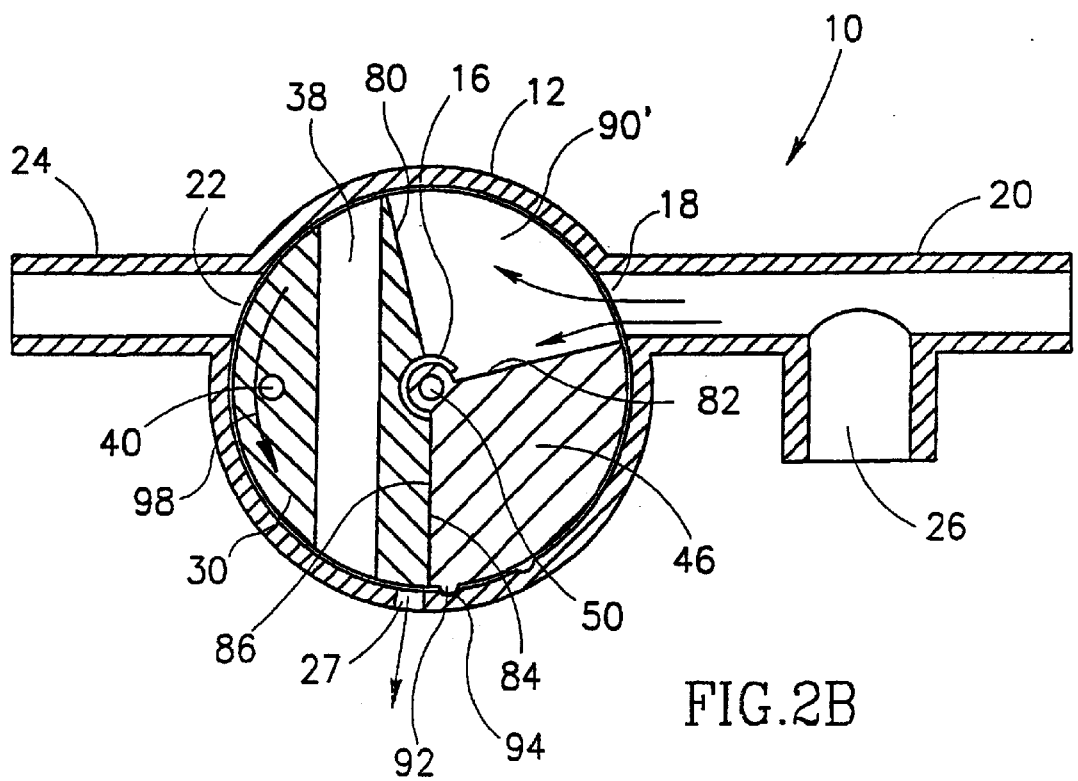
Figure 2C:
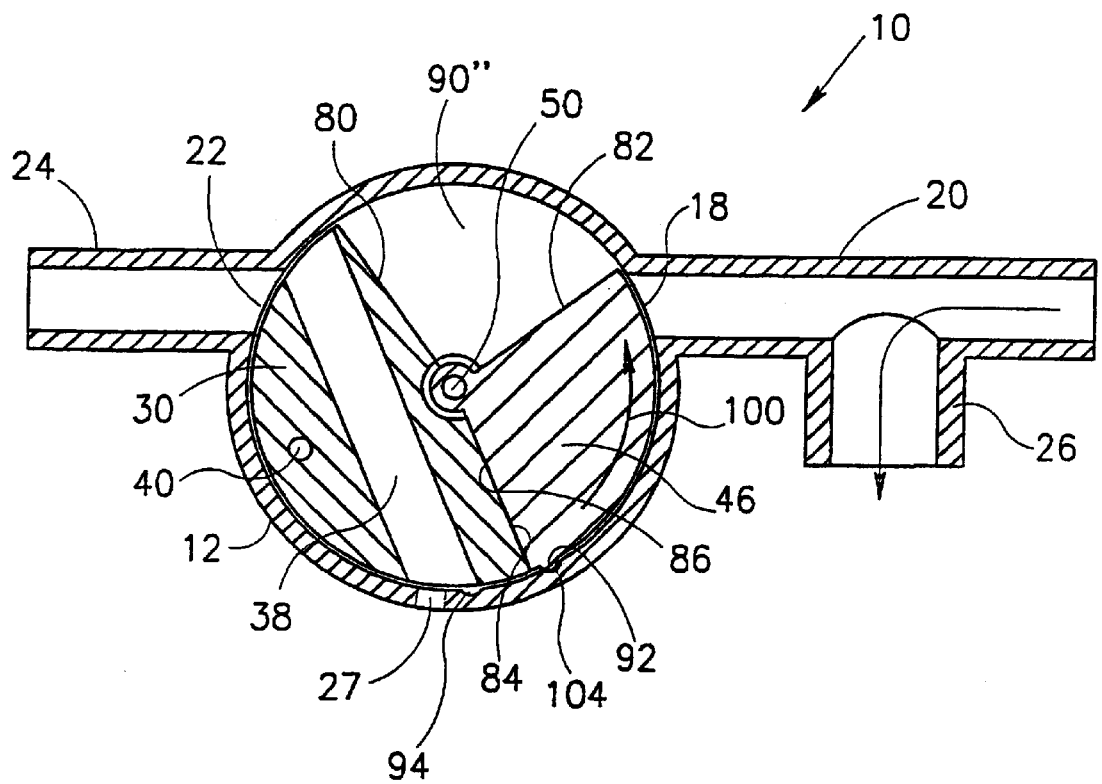

Further attention is now directed to FIGS. 2A and 2C of the drawings illustrating different operative positions of the sampling device.

In the position seen in FIG. 2A, the sampling device is in a so-called flow state wherein the drawing member 30 is in a flow position in which conduit 38 communicates between inlet port 22 and outlet port 18 allowing flow in either direction. However, it will be appreciated that in a specific application tube portion 24 will be connected downstream of an infusion container whereas tube port 20 is connected upstream of an individual, as known per se.

In the position of FIG. 2A, first walls 80 and 82 of the drawing member 30 and the sealing member 46, respectively, are in flush engagement wherein a confined volume 90 is aired via airing port 27 in housing 12.

Further seen in this position, sealing member 46 is snap-engaged in this first position by means of bulge 92 (see also FIG. 1) snappingly received within a first indention 94 formed at an inner wall of housing 12.

When it is desired to take a blood sample from the individual, said drawing member 30 is rotated in a counter-clockwise direction represented by arrow 98 in FIG. 2B by means of the displacing element 56 (not shown) whereby the confined volume 90 of FIG. 2A now moves to a new location indicated by 90' in FIG. 2B. Gradually, as the drawing member 30 is rotatably displaced in the position seen in FIG. 2B a vacuum is generated and liquid contained within tube portions 20 is drawn into confined volume 90'.

It will be appreciated that the confined volume is so calculated as to be sufficiently large to draw the entire amount of liquid contained within tube portion extending between outlet port 18 and the individual (such a volume may typically be in the range of about up to 10 cc).

Referring now to FIG. 2C, the sampling device 10 is illustrated in a position in which the sealing member 46 is displaced into its second position by further rotating the drawing member 30 in direction of arrow 100. In its second position, the sealing member 46 seals the outlet 18. In this position, the confined space 90" is sealed from the outlet tubing 20, the latter containing only fresh blood which may then be drawn through sampling port 26 e.g. by a suitable syringe as known per se.

It is noted that sealing member 46 is retained in its second position, i.e. the sealing position, by means of bulge 92 snappingly received within recess 104 within housing 12.

Upon completing the blood sampling procedure, the drawing member 30 may be rotated back into its initial position as in FIG. 2A consequently displacing sealing member 46 into its corresponding initial position whereby flow in direction of inlet 22 to outlet 18 is resumed.

Figure 3A:
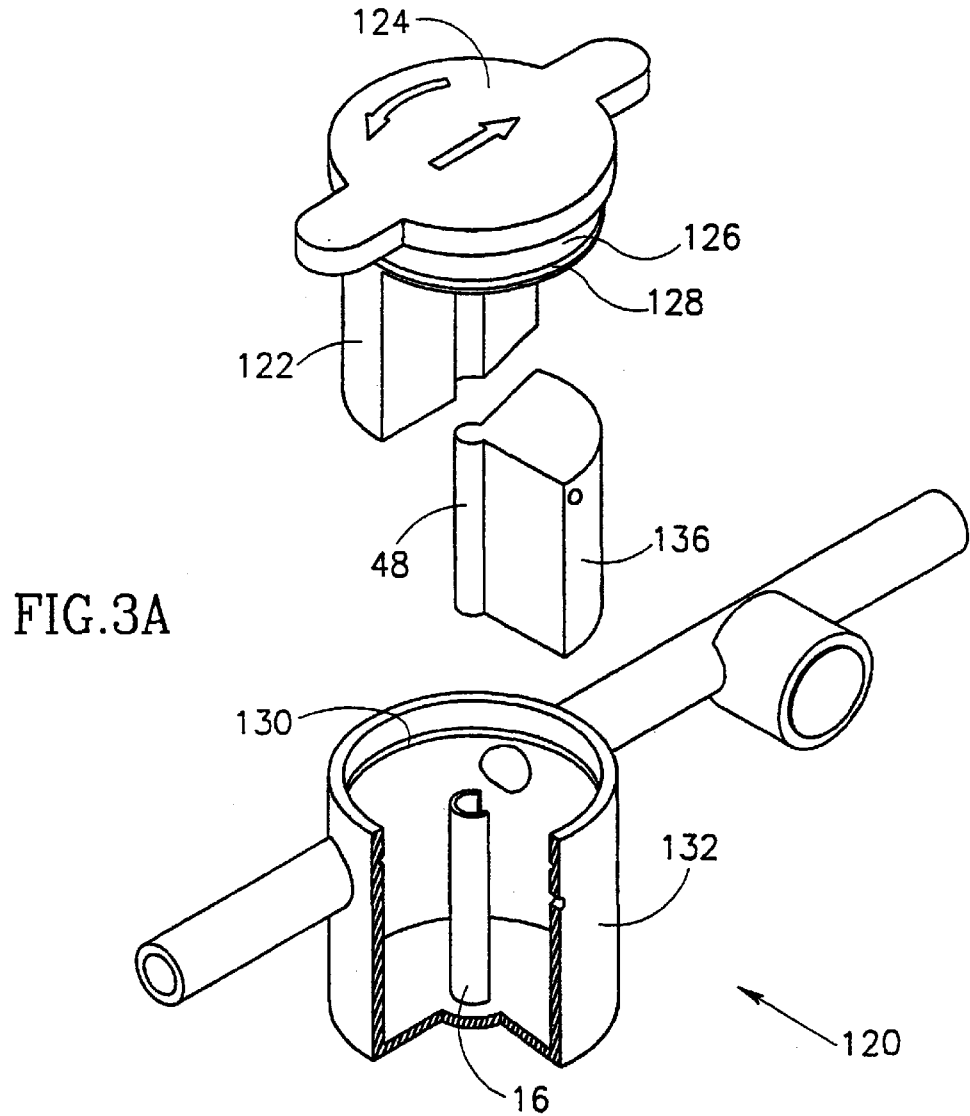
FIG. 3A is a perspective exploded view of a sampling device in accordance with an embodiment of the invention.
Figure 3B:
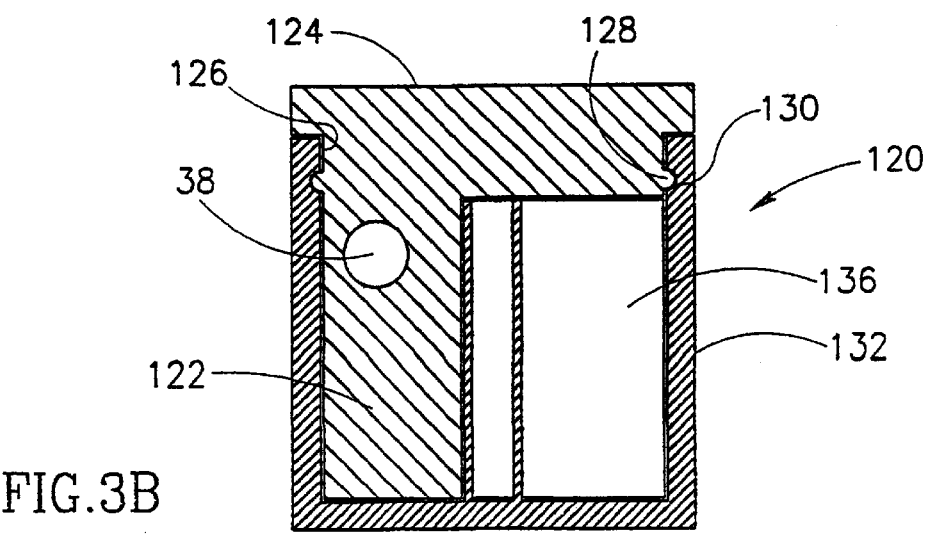
FIG. 3B is a longitudinal cross-section through a device in accordance with FIG. 3A in an assembled position.

Further reference is now being made to FIGS. 3A and 3B which illustrate a second embodiment of the sampling device of the present invention generally designated 120. For the sake of clarity, elements which are essentially similar to elements described with reference to FIGS. 1 and 2 are given like reference numbers.

In accordance with this embodiment, the drawing member 122 is integrally formed with the displacing element 124, eliminating the need of pins 62 and 60 of the previous embodiment. Displacing element 124 comprises a downward extending circular wall portion 126 formed with an annular rim 128 adapted for snappingly engaging with annular groove 130 formed in housing 132.

Sealing member 136 is similar to sealing member 46 in the previous embodiment and may or may not comprise bore 50.

Apart from circumferential recess 130, housing 132 is similar to housing 12 of FIGS. 1 and 2. As can be seen in FIG. 3B, and as can be understood from FIG. 3A, sealing member 136 is swingingly received within housing 132 by rotational engagement of hub portion 48 within hub portion 16 of housing 132. The arrangement, similar as to the previous embodiment, is such that rotational displacement of displacing element 124 brings about also displacement of the drawing member 122 entailing respective displacement of sealing member 136 as explained in connection with FIGS. 2A–2C.

It will be appreciated that the snap engagement of the displacing element 124 within housing 132 provides also sealing engagement so as to prevent leakage from the confined volume.

Figure 4:
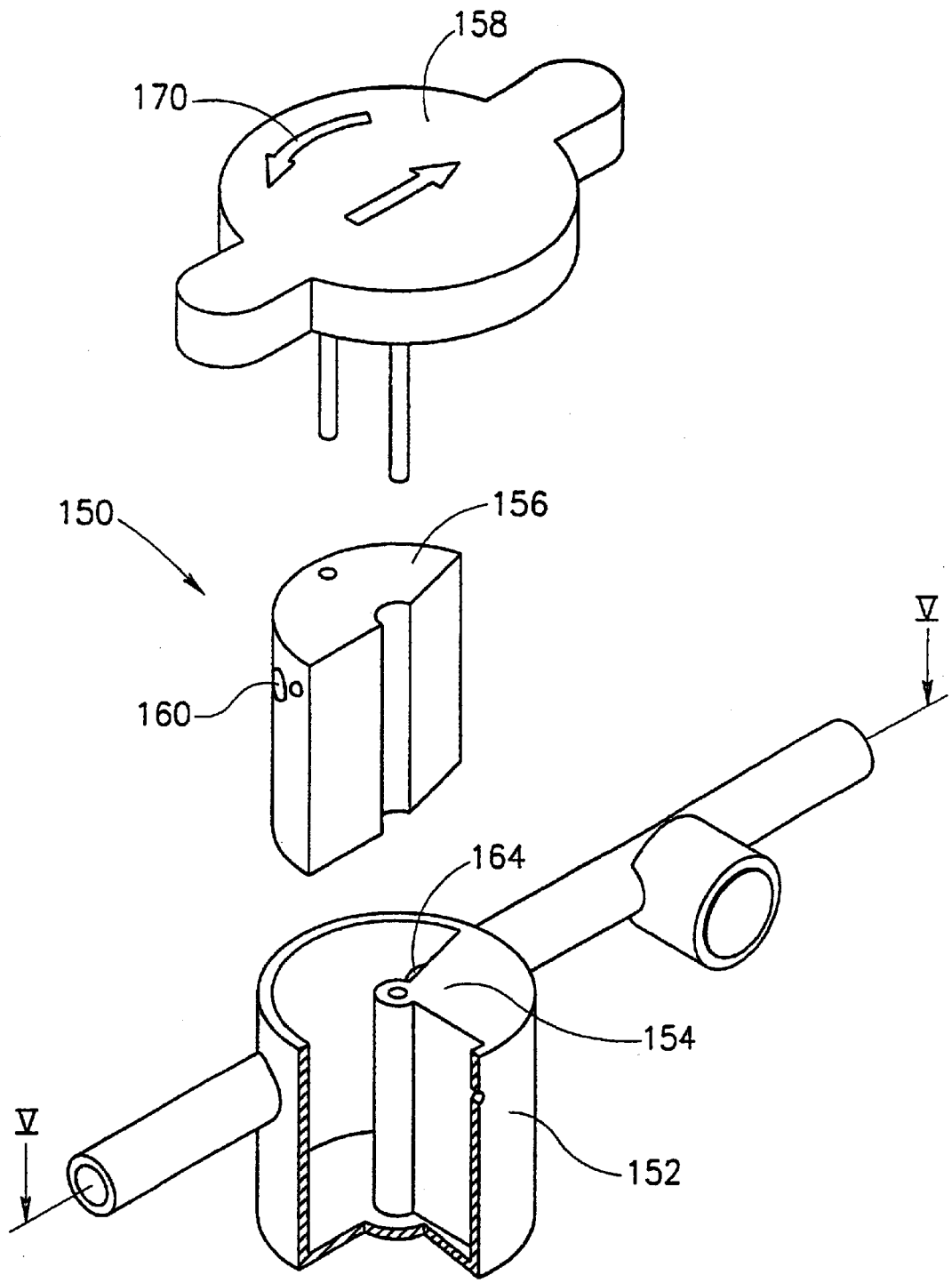
FIG. 4 is a perspective exploded view of a blood sampling device in accordance with an embodiment of the invention.
Figure 5A:
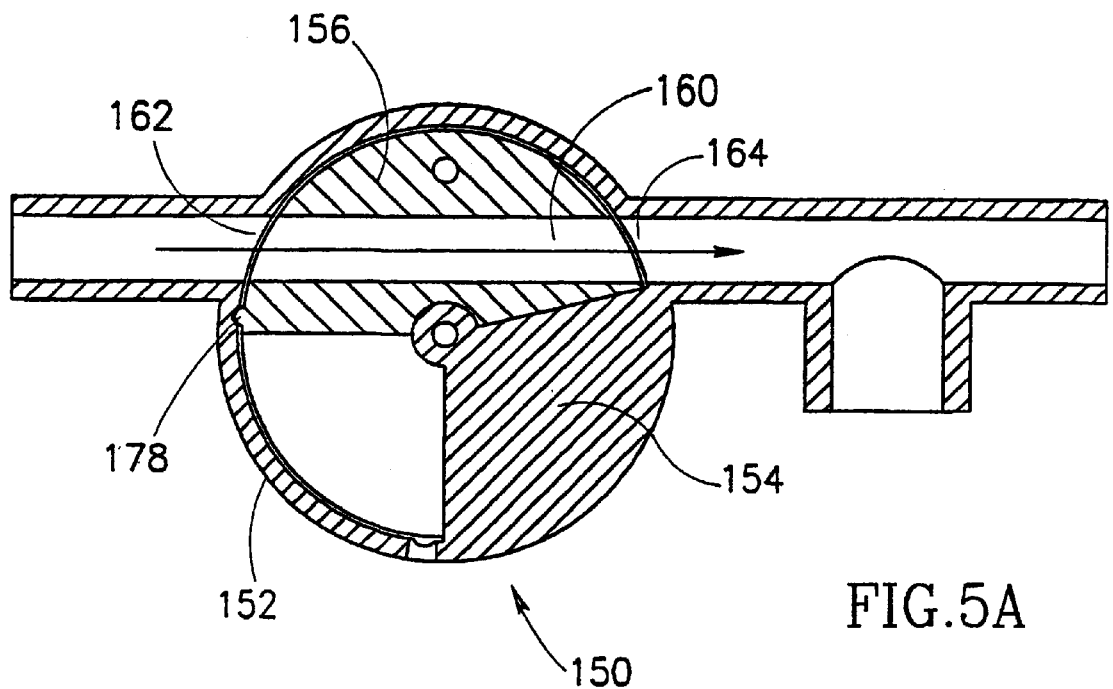
Figure 5B:
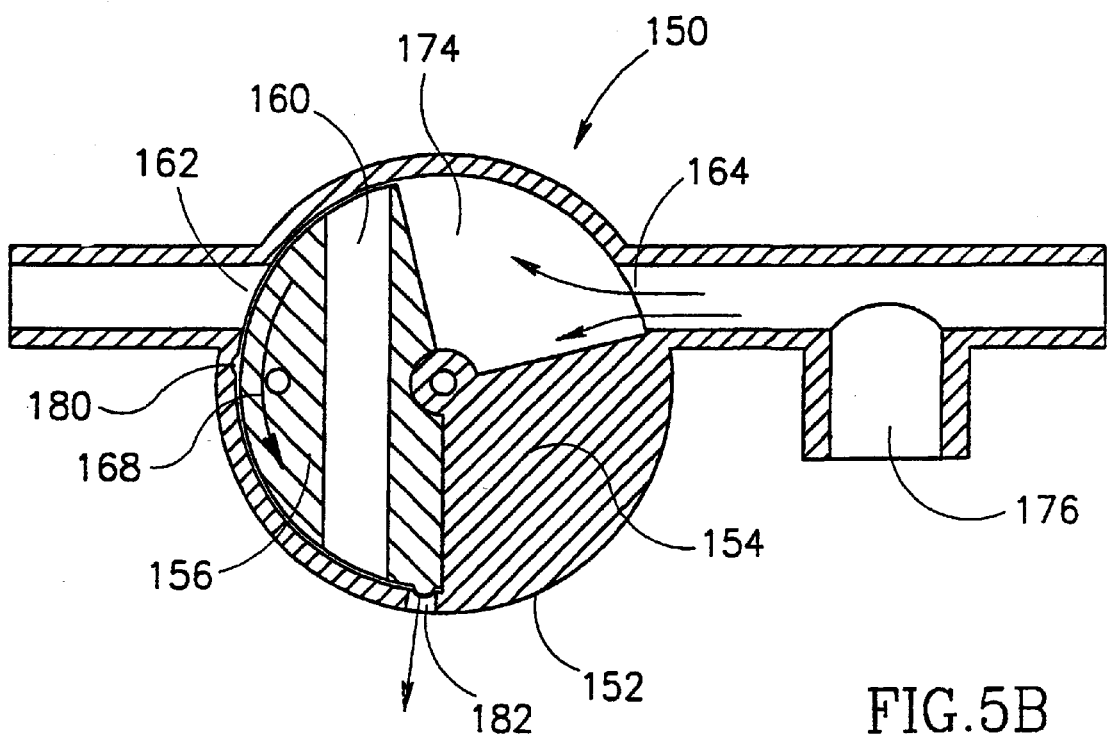

Further attention is now directed to FIGS. 4 and 5 illustrating another embodiment in accordance with the present invention. The device is generally designated 150 and it comprises a housing 152 integrally fitted with a fixed sectorial portion 154 located in the position of sealing member 46 (FIGS. 1 and 2) in its first position. Apart from that, sampling device 150 is similar to sampling device 10 of the embodiment seen in FIGS. 1 and 2 and comprises a drawing member 156, a manipulating member 158, the former being formed with a through-going conduit 160 connecting between an inlet portion 162 and an outlet port 164 of housing 152. It will be appreciated that manipulation of the sampling device 150 is essentially similar to that of the embodiment seen in FIGS. 1 and 2.

The embodiment of FIGS. 4 and 5 differs from the previous embodiments in that it is devoid of a sealing member. In the flow position seen in FIG. 5, conduit 160 is aligned with the inlet and outlet ports 162 and 164, respectively, corresponding with the position of FIG. 2A. Upon rotation of drawing member 156 in direction of arrow 168 (by manipulation of the displacing member 158 in the direction of arrow 170 (FIG. 4) a vacuum is generated within confined volume 174, entailing drawing of liquid into that volume. Thereupon, liquid may be drawn through sampling port 172, e.g. by a syringe or the like. Alternatively, sampling port 176 may comprise a sampling valve of the type which is normally designed to allow flow therethrough and which in a sampling position permits drawing blood only from a pre-selected direction (downstream in the present application).

It will further be noted that the drawing member 156 is fitted with a radial bulge 178 for snap engagement into recesses 180 and to venting port 182, respectively, (see FIG. 5B) for positioning of the drawing member in either of its flow position or drawing position, respectively.

What is claimed is:

1. A liquid sampling device comprising:
   a housing 12 defining a confined volume 90 and fitted with an inlet port 22 and an outlet port 18;
   a drawing member 30 formed with a conduit 38 and being displaceable between a flow position in which said conduit 38 communicates between the inlet port 22 and the outlet port 18, and a drawing position in which communication between the inlet port 22 and the outlet port 18 is interfered and wherein upon displacing the drawing member 40 into the drawing position, liquid is drawn into the confined volume 90 via said outlet port 18.

2. A liquid sampling device according to claim 1, further comprising: a sealing member 46 displaceable between a first position corresponding with the flow and drawing positions of the drawing member 30, and a second position in which the confined volume is sealingly disconnected from the outlet port 18.

3. A liquid sampling device according to claim 1, wherein a sampling port 26 is fitted on a tube connected to the outlet port 18.

4. A liquid sampling device according to claim 2, wherein the housing 12 comprises a cylindrical space 34; the drawing member 30 and the sealing member 46 each have a sector-like shape snugly received within the housing 12, the volume of both said drawing member 30 and said sealing member 46 together is less than the volume of the cylindrical space 34.

5. A liquid sampling device according to claim 4, wherein the drawing member 30 and the sealing member 46 are rotatably displaceable within the housing 12 about a common axis coaxial with an axis of the cylindrical space 34 of the housing 12.

6. A liquid sampling device according to claim 4, further comprising a displacing element 56 extending from said housing 12, for displacing the drawing member 30 between its flow position and the drawing position.

7. A liquid sampling device according to claim 6, wherein the displacing element 56 is articulated or integrally formed with the drawing member 30.

8. A liquid sampling device according to claim 4, wherein a retaining arrangement 92:94 is provided between the housing 12 and either or both of the sealing member 46 and the drawing member 30, for retaining either or both in either of their positions.

9. A liquid sampling device according to claim 8, wherein the retaining arrangement is a snapping-type engagement 92:94 formed between a wall of the housing 12 and a respective wall portion of either or both of the sealing member 46 and the drawing member 30.

10. A liquid sampling device according to claim 1, wherein the housing 12 comprises an airing port 27 for venting the confined volume 90 during displacement of the drawing member 30 between its respective positions.

11. A liquid sampling device according to claim 1, wherein the inlet port 22 and the outlet port 18 are coaxially aligned.

12. A liquid sampling device according to claim 1, wherein an axis of the conduit within the drawing member 30 extends at a plane essentially perpendicular to a plane of displacement of the drawing member 30.

13. A liquid sampling device according to claim 4, wherein displacing the sealing member 46 between its first and second positions is obtained by displacing the drawing member 30.

14. A liquid sampling device according to claim 4, wherein at the flow position of the drawing member 30 a first side wall 80 thereof is flush with a first side wall 82 of the sealing member 46; and at the first and second positions of the sealing member 46 a second side wall thereof 86 is flush with a second side wall 84 of the drawing member 30.

15. A liquid sampling device according to claim 6, wherein the displacing element 56 is snappingly articulated to the housing 12.

* * * * *